(12) United States Patent
Lee et al.

(10) Patent No.: US 9,949,851 B2
(45) Date of Patent: Apr. 24, 2018

(54) FIXING MODULE AND MOTION ASSISTANCE APPARATUS INCLUDING THE SAME

(71) Applicant: Samsung Electronics Co., Ltd., Suwon-Si, Gyeonggi-Do (KR)

(72) Inventors: Minhyung Lee, Anyang-si (KR); Hyun Do Choi, Yongin-si (KR); Jeonghun Kim, Hwaseong-si (KR); Byungjune Choi, Gunpo-si (KR); Se-gon Roh, Suwon-si (KR); Youn Baek Lee, Yongin-si (KR); Jongwon Lee, Uiwang-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 585 days.

(21) Appl. No.: 14/577,931

(22) Filed: Dec. 19, 2014

(65) Prior Publication Data

US 2016/0015532 A1  Jan. 21, 2016

(30) Foreign Application Priority Data

Jul. 17, 2014  (KR) ........................ 10-2014-0090165

(51) Int. Cl.
*A61H 1/00* (2006.01)
*A61F 2/70* (2006.01)
(Continued)

(52) U.S. Cl.
CPC ............... *A61F 2/70* (2013.01); *A61H 1/024* (2013.01); *A61H 1/0244* (2013.01); *A61H 1/0266* (2013.01); *A61H 1/0277* (2013.01); *A61H 1/0281* (2013.01); *A61H 1/0285* (2013.01); *A61H 3/00* (2013.01); *A61H 2201/0192* (2013.01); *A61H 2201/1215* (2013.01);
(Continued)

(58) Field of Classification Search
CPC ....... A61F 2/70; A61H 1/0266; A61H 1/0281; A61H 1/0277; A61H 1/0285; A61H 1/0244; A61H 3/00; A61H 1/024; A61H 2201/164; A61H 2201/1628; A61H 2201/0192; A61H 2201/1215; A61H 2201/165; A61H 2201/5007
See application file for complete search history.

(56) References Cited

U.S. PATENT DOCUMENTS 6,589,195 B1 * 7/2003 Schwenn .............. A61F 5/0125
   602/16
7,416,538 B2   8/2008 Katoh et al.
(Continued)

FOREIGN PATENT DOCUMENTS

EP    2231096 A2   9/2010
JP    2005000634 A   1/2005
(Continued)

*Primary Examiner* — Steven Douglas
(74) *Attorney, Agent, or Firm* — Harness, Dickey & Pierce, P.L.C.

(57) ABSTRACT

Provided are a fixing module and a motion assistance apparatus including the same, the fixing module including a base body, a plurality of side frames provided on both sides of the base body, and a height adjustment assembly provided on the base body, and on which a driving module is mounted to provide a power, wherein a distance between the plurality of side frames may be adjustable.

17 Claims, 8 Drawing Sheets

(51) Int. Cl.
*A61H 1/02* (2006.01)
*A61H 3/00* (2006.01)

(52) U.S. Cl.
CPC .. *A61H 2201/164* (2013.01); *A61H 2201/165* (2013.01); *A61H 2201/1628* (2013.01); *A61H 2201/5007* (2013.01)

(56) References Cited

U.S. PATENT DOCUMENTS

| | | | | |
|---|---|---|---|---|
| 7,628,766 | B1* | 12/2009 | Kazerooni | A61F 5/00 601/35 |
| 7,780,616 | B2 | 8/2010 | Katoh et al. | |
| 8,652,075 | B2 | 2/2014 | Takahashi et al. | |
| 2007/0010378 | A1* | 1/2007 | Katoh | A61F 5/0102 482/105 |
| 2011/0201978 | A1* | 8/2011 | Jeon | A61G 5/045 601/35 |
| 2011/0264014 | A1* | 10/2011 | Angold | B66D 3/18 601/35 |
| 2013/0226048 | A1* | 8/2013 | Unluhisarcikli | A61H 3/00 601/34 |
| 2013/0303950 | A1* | 11/2013 | Angold | B25J 9/0006 601/35 |
| 2014/0330431 | A1* | 11/2014 | Hollander | B25J 9/0006 700/245 |
| 2014/0358053 | A1* | 12/2014 | Triolo | A61H 3/00 602/16 |
| 2015/0209215 | A1* | 7/2015 | Lee | A61H 1/0237 623/27 |

FOREIGN PATENT DOCUMENTS

| | | |
|---|---|---|
| JP | 2006075226 A | 3/2006 |
| JP | 2009284919 A | 12/2009 |
| JP | 2014508010 A | 4/2014 |
| KR | 20080000789 A | 1/2008 |
| KR | 100822375 B1 | 4/2008 |
| KR | 20110103530 A | 9/2011 |
| KR | 101142240 B1 | 5/2012 |
| KR | 101358943 B1 | 2/2014 |

* cited by examiner

FIXING MODULE AND MOTION ASSISTANCE APPARATUS INCLUDING THE SAME

CROSS-REFERENCE TO RELATED APPLICATION

This application claims the priority benefit of Korean Patent Application No. 10-2014-0090165, filed on Jul. 17, 2014, in the Korean Intellectual Property Office, the entire disclosure of which is incorporated herein by reference.

BACKGROUND

1. Field

Example embodiments relate to a fixing module and/or a motion assistance apparatus including the same.

2. Description

With the onset of a rapidly aging society, an increase number of people may experience inconvenience and agony from joint problems, and, therefore, there may be an increased interest in a motion assistance apparatus to assist these people with walking. In addition, motion assistance apparatuses that may increase a muscular strength of a human body are being developed for military purposes.

In general, a motion assistance apparatus may include one or more of a body frame disposed on a trunk of a user, a pelvic frame coupled to a lower side of the body frame to cover a pelvis of the user, a femoral frame disposed on a thigh of the user, a sural frame disposed on a calf of the user, and a pedial frame disposed on a foot of the user. The pelvic frame and the femoral frame may be connected rotatably by a hip joint portion, the femoral frame and the sural frame may be connected rotatably by a knee joint portion, and the sural frame and the pedial frame may be connected rotatably by an ankle joint portion.

The motion assistance apparatus may include an active joint structure including a hydraulic system and/or a driving motor to drive each joint portion to improve a muscular strength of a leg of the user. For example, two motors may be provided at both hip joint portions to transmit a driving power.

SUMMARY

Some example embodiments relate to a fixing module.

In some example embodiments, the fixing module may include a base body, a plurality of side frames provided on both sides of the base body, and a height adjustment assembly provided on the base body, and on which a driving module is mounted to provide a power. A distance between the plurality of side frames may be adjustable.

The plurality of side frames may be provided to move in a horizontal direction with respect to a center of the base body, and the height adjustment assembly may guide the driving module to move in a vertical direction.

The height adjustment assembly may include a guide rail provided on the base body, and a guide plate provided to slidingly move along the guide rail.

The guide plate may include a rotation preventing portion provided to prevent rotation of the guide rail with respect to the guide plate.

The height adjustment assembly may further include a separation preventing member provided to penetrate through the guide rail to be fastened to the guide plate.

The rotation preventing portion may be provided to protrude from one surface of the guide plate to correspond to an outer side surface of the guide rail.

The guide rail may include a guide slot through which a portion of the separation preventing member is to penetrate, and a guide groove provided to be stepped in a periphery of the guide slot.

The rotation preventing portion may be provided to cover at least a portion of a circumference of the guide rail.

The rotation preventing portion may include a fixing hole through which at least a portion of the separation preventing member is to penetrate, and a stepped portion provided to be stepped in a periphery of the fixing hole.

Each side frame may include a frame body provided using a flexible material.

The side frame may further include a reinforcing material disposed at a portion of the side frame at which each corresponding joint assembly is to be provided.

The reinforcing material may be disposed to be long in a height direction of the side frame.

The side frame may further include an internal pad disposed in front of an inner side surface of the side frame, and provided in a shape corresponding to an iliac crest of a human or an animal.

At least a portion of a top of the side frame may be recessed inward.

Other example embodiments relate to a motion assistance apparatus.

In some example embodiments, the motion assistance apparatus may include a fixing module including a plurality of side frames having an adjustable distance therebetween, a plurality of joint assemblies provided on the respective side frames, a driving module movably provided on the fixing module, and a plurality of power transmitting members provided to transmit power from the driving module to the respective joint assemblies.

The driving module may be provided to move in a direction perpendicular to a distance adjustment direction of the side frames.

A height of the driving module mat decrease in response to an increase in a distance between the plurality of side frames, and the height of the driving module may increase in response to a decrease in the distance between the plurality of side frames.

The plurality of side frames may be disposed to be mutually symmetric based on the driving module.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components of the present invention. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Figure 1:
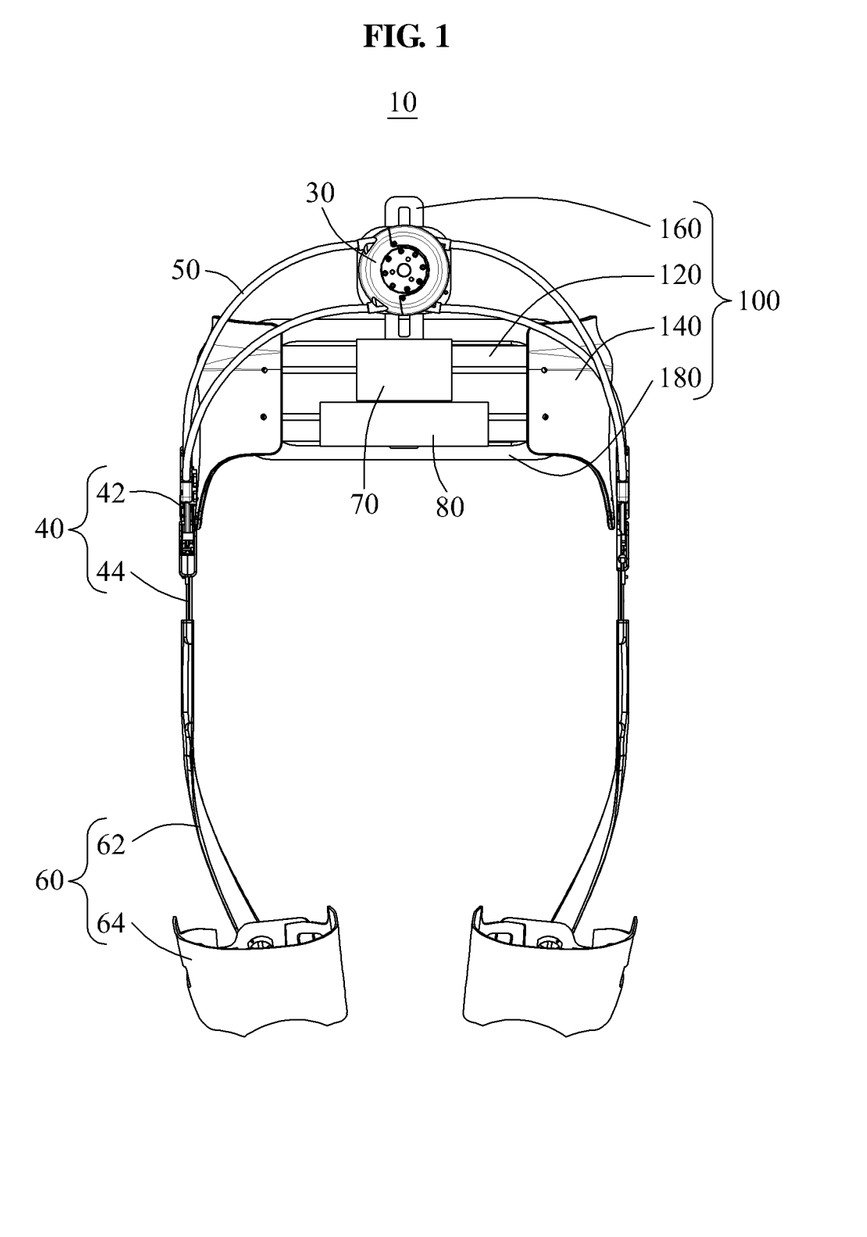
FIG. 1 is a rear view illustrating a motion assistance apparatus according to some example embodiments.
Figure 2:
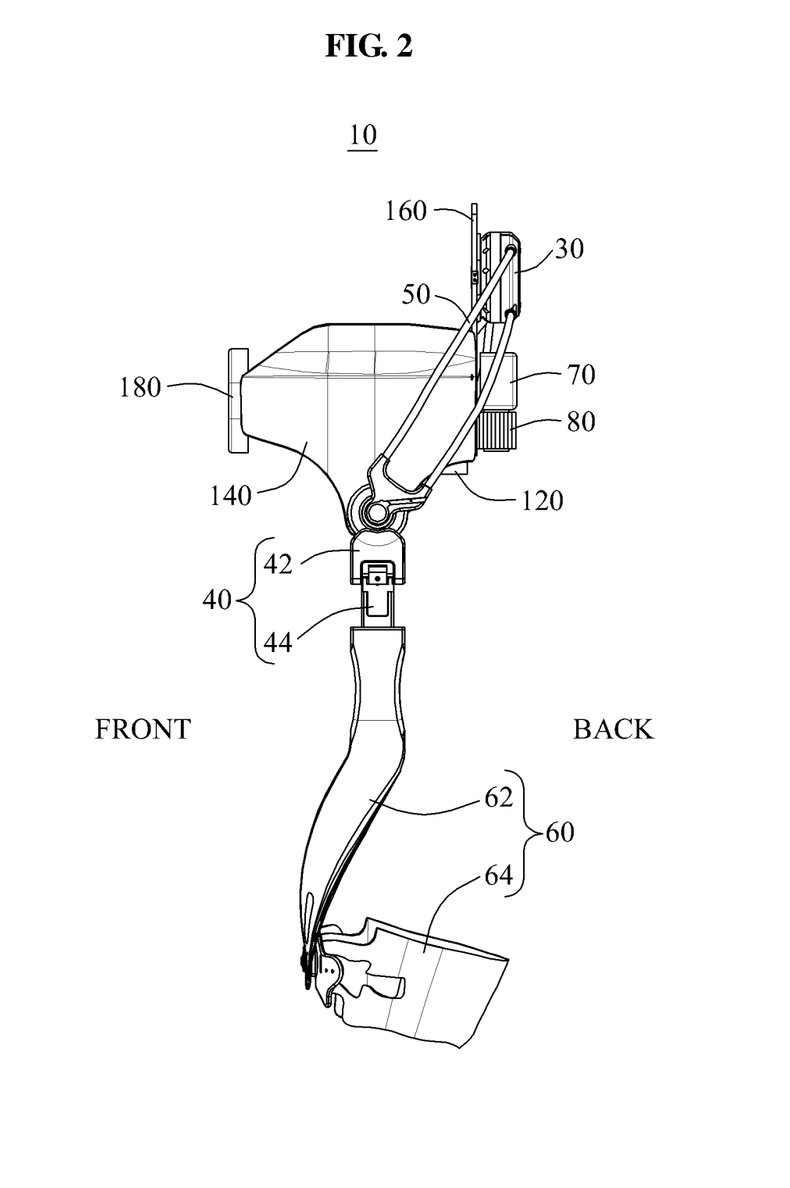
FIG. 2 is a side view illustrating a motion assistance apparatus according to some example embodiments.
Figure 3:
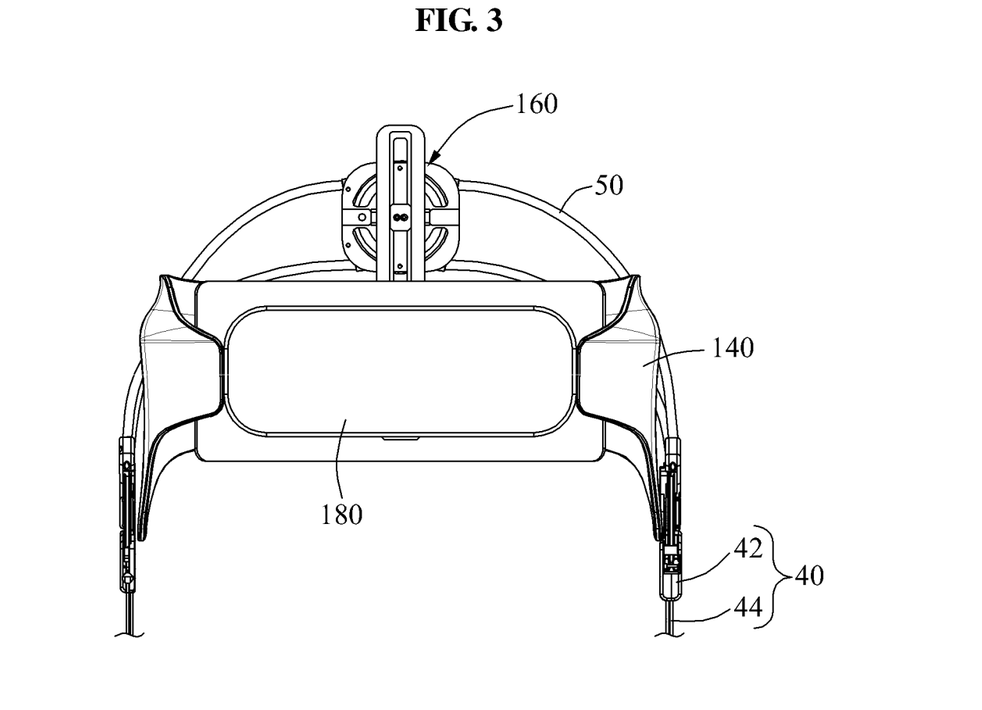
FIG. 3 is a front view illustrating a motion assistance apparatus according to some example embodiments.

FIG. 1 is a rear view illustrating a motion assistance apparatus 10 according to some example embodiments, FIG. 2 is a side view illustrating the motion assistance apparatus 10 according to some example embodiments, and FIG. 3 is a front view illustrating the motion assistance apparatus 10 according to some example embodiments.

Referring to FIGS. 1 through 3, the motion assistance apparatus 10 may be worn on a wearer to assist a motion of the wearer. The wearer may correspond to a human, an animal, or a robot, however, example embodiments are not limited thereto. In addition, although FIG. 1 illustrates a case in which the motion assistance apparatus 10 assists a motion of a thigh of the wearer, the motion assistance apparatus 10 may also assist a motion of a part of an upper body of the wearer, for example, a hand, an upper arm, and a lower arm of the wearer, or a motion of another part of the lower body of the wearer, for example, a foot, and a calf of the wearer. The motion assistance apparatus 10 may assist a motion of a part of the wearer.

Hereinafter, a case in which the motion assistance apparatus 10 assists a motion of a thigh of a human will be described.

The motion assistance apparatus 10 may include a fixing module 100, a driving module 30, a joint assembly 40, a power transmitting module 50, a supporting module 60, a controller 70 to control the driving module 30, and a power supply 80 to supply a power to the driving module 30.

The fixing module 100 may be fixed to the wearer. The fixing module 100 may be in contact with at least a portion of an outer surface of the wearer, and provided in a form of covering the portion of the outer surface of the wearer. The fixing module 100 may include a curved surface to be in contact with the wearer. For example, the fixing module 100 may be fixed to a waist of the wearer.

The fixing module 100 may include a base body 120, a plurality of side frames 140, a height adjustment assembly 160, and a connecting body 180. A circumference of a portion of the wearer may be covered by the base body 120, the side frames 140, and the connecting body 180.

The base body 120 may support one side of the wearer. For example, the base body 120 may support a rear surface of the wearer. The base body 120 may connect the plurality of side frames 140.

The connecting body 180 may support another side of the wearer. For example, the connecting body 180 may support a front surface of the wearer. The connecting body 180 may be provided on an opposite side of the base body 120. The connecting body 180 may connect the plurality of side frames 140.

The plurality of side frames 140 may be provided on both sides of the wearer. For example, the side frames 140 may support left and right sides of the waist of the wearer. The plurality of side frames 140 may include a left frame to support the left side of the wearer, and a right frame to support the right side of the wearer. The plurality of side frames 140 may be provided in shapes corresponding to the left and right sides of the waist of the wearer. The plurality of side frames 140 may be disposed to be mutually symmetric based on the driving module 30.

A distance between the plurality of side frames 140 may be adjustable. The plurality of side frames 140 may move close to and/or move away from each other with respect to a center of the base body 120 or the connecting body 180. Thus, an overall width of the fixing module 100 may be adjusted. In this example, despite a change of the wearer, the same fixing module 100 may be used.

The plurality of side frames 140 may be provided slidingly with respect to the base body 120 and/or the connecting body 180. In an example, the plurality of side frames 140 may be connected to each other by a string member (e.g. one or more cables). By tightening or loosening the string member, the distance between the plurality of side frames 140 may be adjusted. In other example embodiments, the plurality of side frames 140 may include a length-adjustable hook-and loop-fastening member. By changing a fastening position of the hook-and loop-fastening member, the distance between the plurality of side frames 140 may be adjusted. In still other example embodiments, the base body 120 and/or the connecting body 180 may include an elastic body. By lengthening the base body 120 and/or the connecting body 180 to correspond to the circumference of the waist and/or hips of the wearer, the distance between the plurality of side frames 140 may be adjusted.

The height adjust assembly 160 may be provided on one side of the base body 120. The height adjustment assembly 160 may extend from the base body 120 in an upper direction. The driving module 30 may be movably provided on the height adjustment assembly 160. The height adjustment assembly 160 may guide the driving module 30 to move in a vertical direction.

The driving module 30 may provide power to the joint assembly 40. The driving module 30 may be disposed to be spaced apart from the joint assembly 40, and on an opposite side of the joint assembly 40 with respect to the base body 120. The driving module 30 may be movably provided on the fixing module 100. The driving module 30 may be a motor configured to receive a voltage or a current from the power supply 80 and to generate the power.

The joint assembly 40 may receive the power from the driving module 30 to assist a motion of a joint portion of the wearer. The joint assembly 40 may be disposed at a position corresponding to the joint portion of the wearer. The joint assembly 40 may be disposed on each of the plurality of side frames 140. One side of the joint assembly 40 may be connected to the power transmitting module 50, and another side of the joint assembly 40 may be connected to the supporting module 60.

The joint assembly 40 may include a rotating member 42 and a connecting member 44.

The rotating member 42 may rotate in response to the power received from the power transmitting module 50 to generate a torque. The rotating member 42 may be disposed on one or more sides of a hip joint of the wearer.

The connecting member 44 may connect the rotating member 42 to the supporting module 60. The connecting member 44 may rotate by the torque of the rotating member 42. The connecting member 44 may be fastened to the rotating member 42 by a separate fastening member, or provided to be integrated with the rotating member 42. The connecting member 44 may be connected to the supporting module 60 in a hinge connection structure. The supporting module 60 may perform a two degree of freedom (DOF) motion with respect to the fixing module 100 by means of an axis of rotation of the rotating member 42 and a hinge axis of the hinge connection structure.

A DOF may mean the number of independent motions of a mechanism, or the number of independent parameters that are required to specify an independent motion at a relative position with respect to links.

The power transmitting module 50 may transmit the power from the driving module 30 to the joint assembly 40. The power transmitting module 50 may include a power transmitting member, and a tube to cover the power transmitting member.

The power transmitting member may transmit the power using a pushing or pulling force, or transmit the power using a frictional force, a tensile force, or an elastic force. For example, the power transmitting member may include a wire, a cable, a string, a rubber band, a spring, a belt, and a chain. A power input terminal of the power transmitting member may be connected to the driving module 30, and a power output terminal of the power transmitting member may be connected to the rotating member 42. The power transmitting member may move within the tube.

The tube may include a flexible material such as, for example, rubber, and silicone. In other example embodiments, the tube may have a structure in which a plurality of segments are fluidly connected to each other. Thus, the entire tube may have flexibility. The tube may prevent direct contact between the power transmitting member and the wearer, thereby increasing a user wearability and a durability of the power transmitting member.

The supporting module 60 may support a portion of the wearer. The supporting module 60 may assist a motion of the portion of the wearer. The supporting module 60 may rotate by the power received from the joint assembly 40. The torque of the supporting module 40 may be transmitted to a portion of the wearer to assist a motion of the portion of the wearer. The supporting module 60 includes a supporting frame 62 rotatably connected to the joint assembly 40, and a supporting member 64 to cover a portion of the wearer.

The controller 70 may include a processor and a memory (not shown).

The processor may be an arithmetic logic unit, a digital signal processor, a microcomputer, a field programmable array, a programmable logic unit, a microprocessor or any other device capable of responding to and executing instructions in a defined manner such that the processor is programmed with instructions that configure the controller 70 as a special purpose computer to control the driving module 30 and/or the fixing module 100. For example, the controller 70 may control the amount of power provided by the driving module 30 to the joint assembly 40. Further, the controller 70 may instruct the fixing module 10 to adjust a height of the driving module 30.

The memory may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

Figure 4:
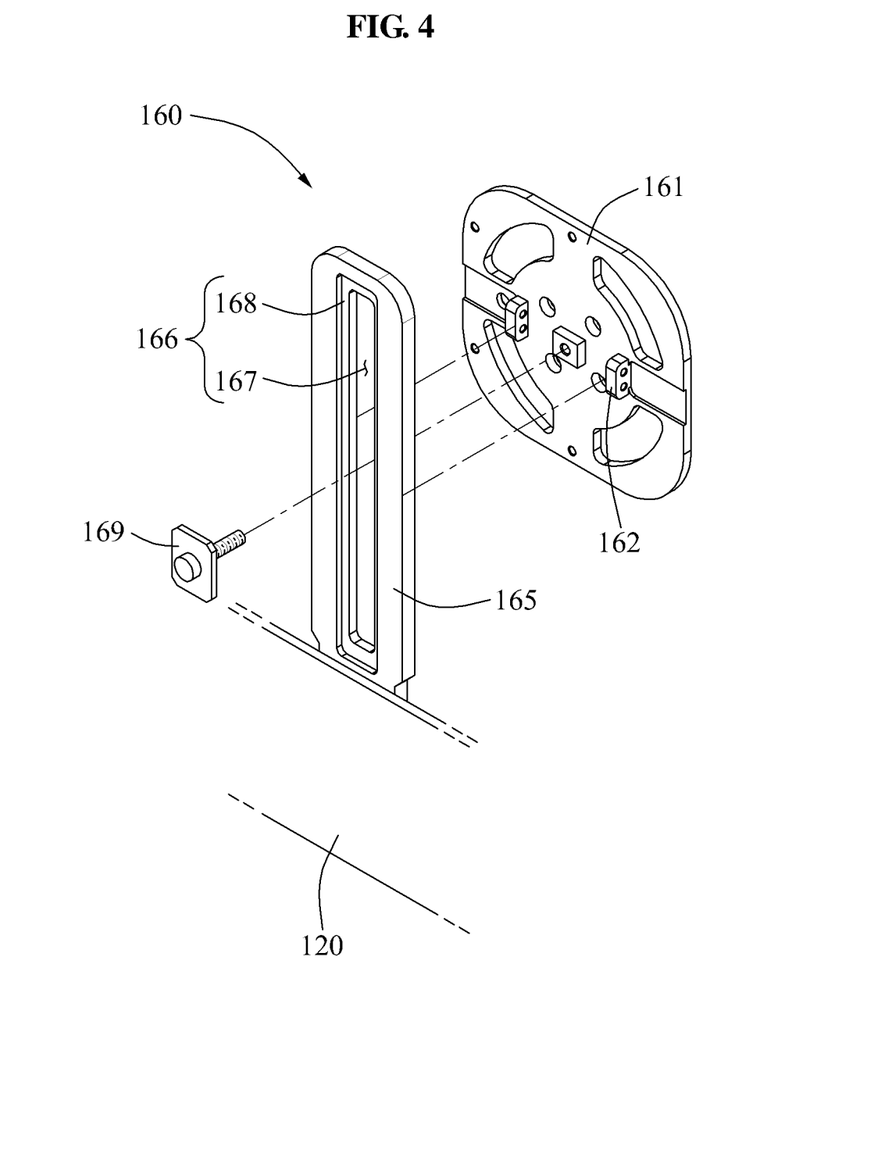
FIG. 4 is an exploded perspective view illustrating a height adjustment assembly according to some example embodiments.

FIG. 4 is an exploded perspective view illustrating the height adjustment assembly 160 according to some example embodiments.

Referring to FIG. 4, the height adjustment assembly 160 may include a guide plate 161, a guide rail 165, and a separation preventing member 169.

The guide plate 161 may be attached to the driving module 30. The guide plate 161 may be provided to be integrated with the driving module 30, or provided as a separate member to be connected to the driving module 30.

The guide plate 161 may be movably provided on the guide rail 165. The guide plate 161 may slide along the guide rail 165. The guide plate 161 includes a rotation preventing portion 162.

The rotation preventing portion 162 may prevent rotation of the guide rail 165 with respect to the guide plate 161. The rotation preventing portion 162 may be one or more protrusions that protrude from one surface of the guide plate 161 to correspond to an outer side surface of the guide rail 165. A plurality of rotation preventing portions 162 may be provided to support both outer side surfaces of the guide rail 165. For example, the rotation prevention portion 162 may include three protrusions that are configured to sit on each side of the guide rail 165 and in a slot in a middle thereof.

The guide rail 165 may guide the guide plate 161. The guide rail 165 may be provided on the base body 120. The guide rail 165 may extend from the base body 120 in an upper direction. The guide rail 165 includes an insertion portion 166.

The insertion portion 166 may receive the separation preventing member 169. The insertion portion 166 includes a guide slot 167 and a guide groove 168. The guide slot 167 may be a hole provided in the guide rail 165. The guide slot 167 may be provided to be long in a longitudinal direction of the guide rail 165. A portion of the separation preventing member 169 may penetrate through the guide slot 167. The guide groove 168 may be provided to be stepped in a periphery of the guide slot 167. A portion of the separation preventing member 169 may be seated in the guide groove 168.

The separation preventing member 169 may prevent a separation between the guide plate 161 and the guide rail 165. The separation preventing member 169 may be one or more screws. The separation preventing member 169 may penetrate through the guide rail 165 to be fastened to the guide plate 161. The separation preventing member 169 includes a portion to penetrate through the guide slot 167, and a portion to be seated in the guide groove 168. The portion to penetrate through the guide slot 167 may be provided in a size equal to or smaller than a width of the guide slot 167, and penetrate through the guide slot 167 to be fixed to the guide plate 161. The portion to be seated in the guide groove 168 may be provided in a size greater than the width of the guide slot 167, and in various forms such as, for example, a rectangular form, and a circular form. In the structure as described above, the guide plate 161 may perform a rectilinear motion along the guide rail 165 without rotating.

Hereinafter, an operation of the fixing module 100 will be described.

The height adjustment assembly 160 may adjust a height of the driving module 30 to correspond to the distance between the plurality of side frames 140. The plurality of side frames 140 may move in a horizontal direction with respect to the center of the base body 120. The height adjustment assembly 160 may guide the driving module 30 to move in a vertical direction. Therefore, the driving module 30 may move in a direction perpendicular to a distance adjustment direction of the side frames 140.

The height of the driving module 30 may be adjusted based on the distance between the plurality of side frame 140. In response to an increase in the distance between the plurality of side frames 140, the height of the driving module 30 may decrease. Conversely, in response to a decrease in the distance between the plurality of side frames 140, the height of the driving module 30 may increase.

For example, in response to an increase in the distance between the plurality of side frames 140, a distance between the driving module 30 and the joint assembly 40 may increase. In this example, a tensile force greater than a reference tensile force may be applied to both sides of the power transmitting module 50. A magnitude of the reference tensile force may not be necessarily greater than "0", and may correspond to "0" or a negative value. In response to the decrease in the height of the driving module 30, the distance between the driving module 30 and the joint assembly 40 may decrease. In response to a sufficient decrease in the height of the driving module 30, a tensile force corresponding to the reference tensile force may be applied to both sides of the power transmitting module 50.

Conversely, in response to a decrease in the distance between the plurality of side frames 140, the distance between the driving module 30 and the joint assembly 40 may decrease. In this example, a tensile force smaller than the reference tensile force may be applied to both sides of the power transmitting module 50. In response to an increase in the height of the driving module 30, the distance between the driving module 30 and the joint assembly 40 may increase. In response to a sufficient increase in the height of the driving module 30, a tensile force corresponding to the reference tensile force may be applied to both sides of the power transmitting module 50.

In summary, by adjusting the height of the driving module 30 to correspond to the distance between the plurality of side frames 140, an appropriate tensile force may be applied to both sides of the power transmitting module 50. Thus, damage to the motion assistance apparatus 10 and an abnormal operation of the motion assistance apparatus 10 caused by an abnormal tensile force applied from the power transmitting module 50 may be prevented.

The height of the driving module 30 may be adjusted automatically by a lateral pressure or a tensile force applied to both sides of the power transmitting module 50. The height of the driving module 30 may also be adjusted manually by a user.

The guide plate 161 may be fixed at a desired (or, alternatively, a predetermined) height. By firmly fixing the separation preventing member 169 to the guide plate 161, the guide plate 161 may not move with respect to the guide rail 165.

Figure 5:
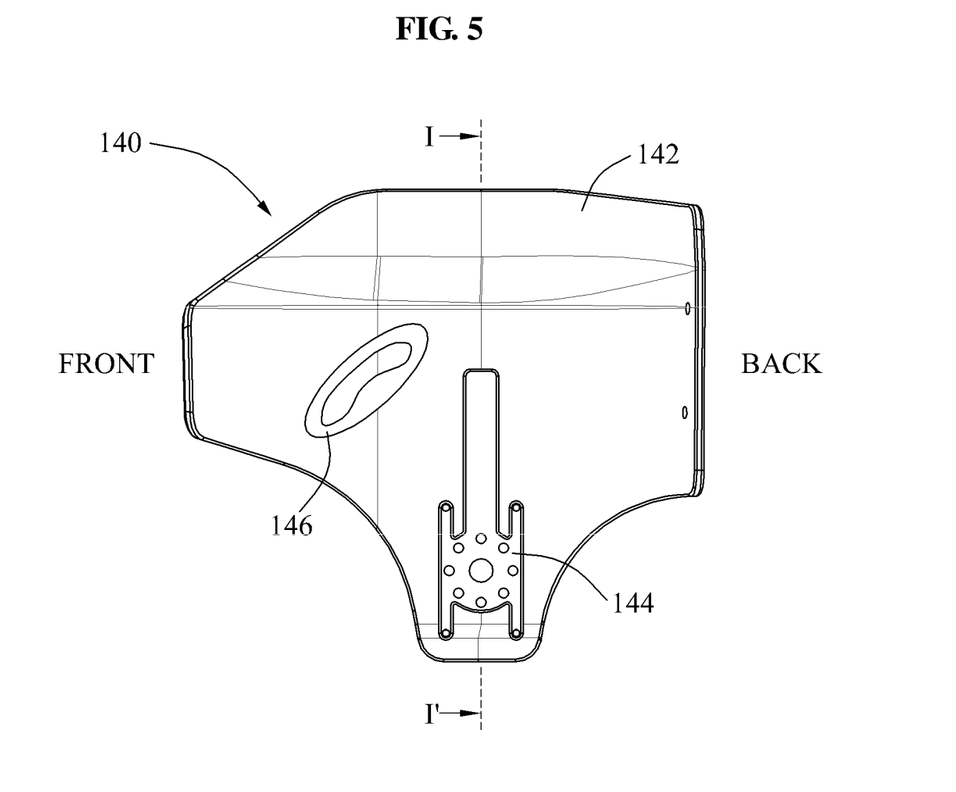
FIG. 5 is a view illustrating an inner side surface of a side frame according to some example embodiments.
Figure 6:
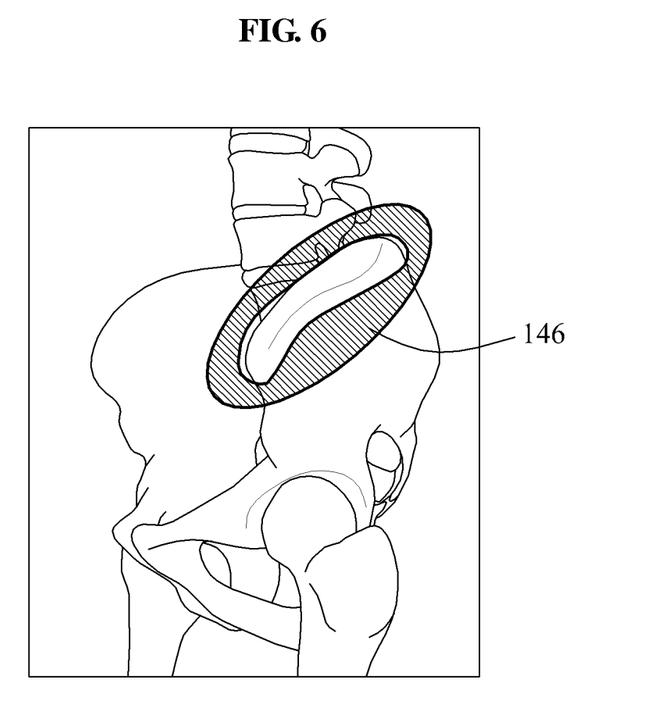
FIG. 6 illustrates an internal pad according to some example embodiments.
Figure 7:
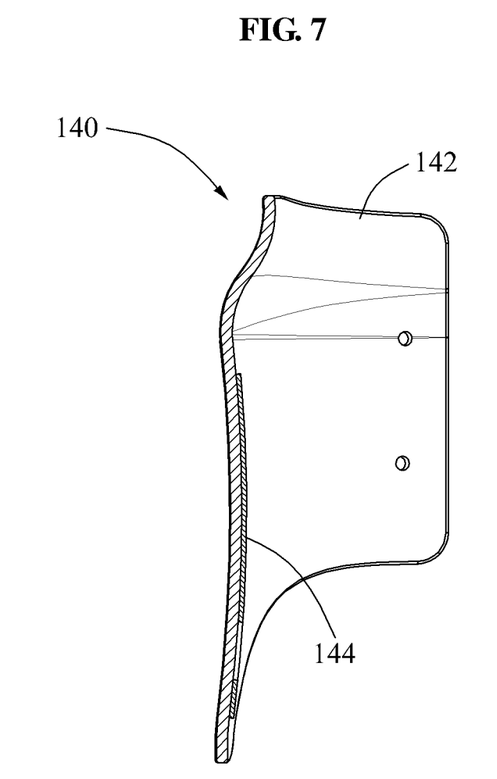
FIG. 7 is a cross-sectional view illustrating the side frame of FIG. 5, cut along a line I-I'.

FIG. 5 is a view illustrating an inner side surface of a side frame 140 according to example embodiments. FIG. 6 illustrates an internal pad 146 according to example embodiments. FIG. 7 is a cross-sectional view illustrating the side frame 140 of FIG. 5, cut along a line I-I'.

Referring to FIGS. 5 through 7, the side frame 140 includes a frame body 142, a reinforcing material 144, and the internal pad 146.

The frame body 142 may form an appearance of the side frame 140. The frame body 142 may be provided in a shape corresponding to a side surface of the wearer. The frame body 142 may include a flexible material. Although a distance between side frames 140 is adjusted, the side frame 140 may be transformed to be in close contact with a circumference of the waist and/or hips of the wearer.

At least a portion of a top of the frame body 142 may be recessed inward. The recessed portion may be stably hung on an upper side of a pelvic portion of the wearer. Thus, a supporting force of the frame body 142 may increase.

The reinforcing material 144 may reduce a shaking of the joint assembly 40. The reinforcing material 144 may be disposed at a portion of the frame body 142 at which the joint assembly 40 is disposed. The reinforcing material 144 may be connected to the joint assembly 40. The reinforcing member 144 may be disposed at a position overlapping a portion most highly protruding toward a side surface of the frame body 142. The reinforcing material 144 may be disposed on an inner side surface or an outer side surface of the frame body 142. The reinforcing material 144 may be disposed in an internal portion of the frame body 142. The reinforcing material 144 may be provided using a material having a higher rigidity than the frame body 142. For example, the reinforcing material 144 may be provided using plastic or metal. The reinforcing material 144 may be disposed to be long in a height direction of the frame body 142. A vertical length of the reinforcing material 144 may be longer than a horizontal length thereof.

When the frame body 142 includes the flexible material, a desired (or, alternatively, a predetermined) position of the joint assembly 40 with respect to the wearer may be maintained by the reinforcing material 144. In addition, according to the shape of the reinforcing material 144, a portion, excluding the portion of the frame body 142 at which the joint assembly 40 is disposed, may have a sufficient flexibility.

The internal pad 146 may be provided in a shape corresponding to an iliac crest of the wearer. For example, the internal pad 146 may include a hole or a recess. The hole or the recess may be provided in a shape corresponding to at least a portion of the iliac crest. For example, the internal pad 146 may be disposed in front of an inner side surface of the frame body 142. The hole or the recess of the internal pad 146 may be provided to incline downward from a rear portion to a front portion. The internal pad 146 may receive the iliac crest of the wearer, thereby increasing a supporting force of the frame body 142.

Hereinafter, the same name may be used to describe an element included in the example embodiments described above and an element having a common function. Unless otherwise mentioned, the descriptions of the above example embodiments may be applicable to the following example embodiments and thus, duplicated descriptions will be omitted for conciseness.

Figure 8:
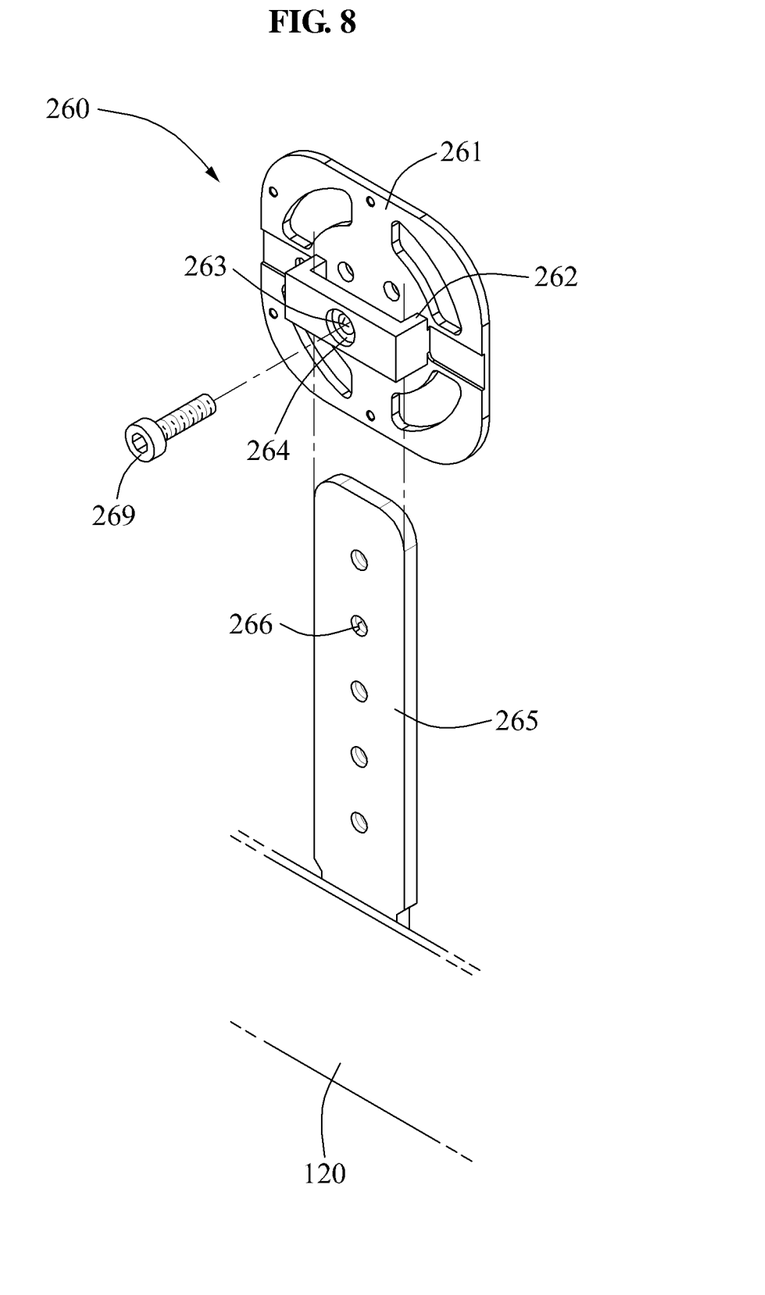
FIG. 8 is an exploded perspective view illustrating a height adjustment assembly according to other example embodiments.

FIG. 8 is an exploded perspective view illustrating a height adjustment assembly 260 according to other example embodiments.

Referring to FIG. 8, the height adjustment assembly 260 may include a guide plate 261, a guide rail 265, and a separation preventing member 269.

The guide plate 261 may fix the driving module 30. The guide plate 261 may be movably provided on the guide rail 265. The guide plate 261 may slide along the guide rail 265. The guide plate 261 may be provided to be integrated with the driving module 30, or provided as a separate member to be connected to the driving module 30. The guide plate 261 includes a rotation preventing portion 262.

The rotation preventing portion 262 may prevent rotation of the guide rail 265 with respect to the guide plate 261. The rotation preventing portion 262 may be provided to cover at least a portion of a circumference of the guide rail 265. The rotation preventing portion 262 includes a fixing hole 263 and a stepped portion 264. The fixing hole 263 may be a hole provided in the rotation preventing portion 262. A portion of the separation preventing member 269 may penetrate through the fixing hole 263. The stepped portion 264 may be provided to be stepped in a periphery of the fixing hole 263. Another portion of the separation preventing member 269 may be seated in the stepped portion 264.

The guide rail 265 may guide the guide plate 261. The geode rail 265 may be provided on the base body 120. The guide rail 265 may extend from the base body 120 in an upper direction. The guide rail 265 includes an insertion portion 266.

The separation preventing member 269 may be inserted into the insertion portion 266. The insertion portion 266 may be a hole provided in the guide rail 265. A plurality of insertion portions 266 may be provided in a longitudinal direction of the guide rail 265. The separation preventing member 269 may be inserted into a portion of the plurality of insertion portions 266 to fix the guide plate 261. Contrary to FIG. 8, the insertion portion 266 may be provided to be long in the longitudinal direction of the guide rail 265.

The separation preventing member 269 may prevent a separation between the guide plate 261 and the guide rail 265. The separation preventing member 269 may be one or more screws. The separation preventing member 269 may penetrate through the rotation preventing portion 262 to be fastened to the guide rail 265. The separation preventing member 269 includes a portion to penetrate through the fixing hole 263, and a portion to be seated in the stepped portion 264. The portion to penetrate through the fixing hole 263 may be provided in a size equal to or smaller than a width of the fixing hole 263, and penetrate through the fixing hole 263 to be fastened to the guide rail 265. The portion to be seated in the stepped portion 264 may be provided in a size greater than the width of the fixing hole 263.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A fixing module configured to attach to a wearer thereof, the fixing module comprising:
    a base body;
    a plurality of side frames configured to connect to at least two sides of the base body such that a distance between the plurality of side frames is adjustable; and
    a height adjustment assembly on the base body, the height adjustment assembly configured to support a driving module, the driving module configured to generate power, the height adjustment assembly including,
        a guide rail on a first one of the base body and the driving module, and
        a guide plate configured to support a second one of the base body and the driving module, the guide plate configured to slidingly move along the guide rail.

2. The fixing module of claim 1, wherein the plurality of side frames are configured to move in a horizontal direction with respect to a center of the base body, and the height adjustment assembly is configured to move the driving module in a vertical direction.

3. The fixing module of claim 1, wherein the guide plate comprises:
    a rotation preventing portion configured to prevent rotation of the guide rail with respect to the guide plate.

4. The fixing module of claim 3, wherein the height adjustment assembly further comprises:
    a separation preventing member configured to penetrate through the guide rail and fasten to the guide plate.

5. The fixing module of claim 4, wherein the rotation preventing portion is provided to protrude from one surface of the guide plate to correspond to an outer side surface of the guide rail.

6. The fixing module of claim 5, wherein the guide rail comprises:
    a guide slot configured to receive a portion of the separation preventing member; and
    a guide groove having a stepped shape in a periphery of the guide slot.

7. The fixing module of claim 4, wherein the rotation preventing portion is provided to cover at least a portion of a circumference of the guide rail.

8. The fixing module of claim 6, wherein the rotation preventing portion comprises:
- a fixing hole configured to receive at least a portion of the separation preventing member; and
- a stepped portion around the fixing hole, the stepped portion corresponding to the guide slot.

9. The fixing module of claim 1, wherein each of the side frames comprise:
- a frame body, the frame body including a flexible material.

10. The fixing module of claim 9, wherein the side frames further comprise:
- a reinforcing material at a portion of the side frames corresponding to a joint assembly which is configured to receive power from the driving module to assist a motion of a joint of the wearer.

11. The fixing module of claim 10, wherein a length of the reinforcing material with respect to the side frames is longer than a width of the reinforcing material.

12. The fixing module of claim 9, wherein the side frames further comprise:
- an internal pad in front of an inner side surface of the side frames, the internal pad having a shape corresponding to an iliac crest of the wearer.

13. The fixing module of claim 9, wherein at least a portion of a top of the side frames is recessed inward.

14. A fixing module configured to attach to a wearer thereof, the fixing module comprising:
- a base body;
- a plurality of side frames configured to connect to at least two sides of the base body such that a distance between the plurality of side frames is adjustable; and
- a height adjustment assembly on the base body, the height adjustment assembly configured to support a driving module, the driving module configured to generate power, wherein
the fixing module is configured to,
    decrease a height of the driving module in response to an increase in the distance between the plurality of side frames, and
    increase the height of the driving module in response to a decrease in the distance between the plurality of side frames.

15. A motion assistance apparatus comprising:
- a fixing module configured to attach to a wearer thereof, the fixing module configured to adjust a distance between a plurality of side frames included therein;
- a plurality of joint assemblies on respective ones of the side frames;
- a driving module configured to move on the fixing module; and
- a plurality of power transmitting members configured to transmit power from the driving module to respective ones of the joint assemblies, wherein the fixing module is configured to adjust the distance between the plurality of side frames in a first direction and move the driving module in a second direction perpendicular to the first direction.

16. The motion assistance apparatus of claim 15, wherein the fixing module is configured to,
    decrease a height of the driving module in response to an increase in the distance between the plurality of side frames, and
    increase the height of the driving module in response to a decrease in the distance between the plurality of side frames.

17. The motion assistance apparatus of claim 15, wherein the plurality of side frames are symmetric with respect to the driving module.

* * * * *